US006837237B2

(12) United States Patent
Kirn

(10) Patent No.: US 6,837,237 B2
(45) Date of Patent: *Jan. 4, 2005

(54) MAGNETIC NASAL TUBE BRIDLE SYSTEM AND RELATED METHOD

(75) Inventor: David S. Kirn, Lexington, KY (US)

(73) Assignee: Kirn Medical Design, L.L.C., Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/628,600

(22) Filed: Jul. 28, 2003

(65) Prior Publication Data

US 2004/0069309 A1 Apr. 15, 2004

Related U.S. Application Data

(63) Continuation of application No. 09/939,399, filed on Aug. 24, 2001, now Pat. No. 6,631,715.

(51) Int. Cl.[7] .............................................. A61M 15/00

(52) U.S. Cl. ............................. 128/200.24; 128/207.14

(58) Field of Search ....................... 126/200.24, 200.26, 126/206.11, 207.14, 207.15, 207.16, 207.18, 912, DIG. 26; 606/108

(56) References Cited

U.S. PATENT DOCUMENTS

| 3,323,208 A | 6/1967 | Hurley, Jr. |
| 3,705,586 A | 12/1972 | Sarracino |
| 3,744,104 A | 7/1973 | Ford |

FOREIGN PATENT DOCUMENTS

| EP | 0 567 029 | 10/1993 |

OTHER PUBLICATIONS

Thomas N. Zweng, MD, FACS; Bradley B. Hill, MD; and William E. Strodel, MD, FACS, An Improved Technique for Securing Nasoenteral Feeding Tubes, Journal of the American College of Surgeons, Sep. 1996, vol. 183.

Marc J. Popovich, MD; John D. Lockrem, MD; and Joel B. Zivot, MD, Nasal Bridle Revisted; An Improvement in the Technique to Prevent Unintentional Removal of Small–Bore Nasoenteric Feeding Tubes, Crit Care Med 1996 vol. 24, No. 3.

Brandt, C.P., Mittendorf, E.A., Endoscopic placement of nasojejunal feeding tubes in ICU patients. Surgical Endoscopy (1999) 13:1211–1214. Springer–Verlag, New York.

Meer, J.A., A New Nasal Bridle for Securing Nasoenteral Feeding Tubes. J. Parenteral and Enteral Nutrition, vol. 13, No. 3 (1989). American Society for Parenteral and Enteral Nutrition.

Barrocas, A., Jastram, C. et al., The Bridle: Increasing the Use of Nasoenteric Feedings. Nutritional Support Services, vol. 2, No. 8, Aug. 1982.

(List continued on next page.)

Primary Examiner—Henry Bennett
Assistant Examiner—Teena Mitchell
(74) Attorney, Agent, or Firm—King & Schickli, PLLC

(57) ABSTRACT

A bridle system for placing and securing a nasal tube in a patient includes a flexible member having a magnet attached to or secured within a first end thereof for insertion into a nare of a patient's nose, and a probe for insertion into a second nare of the nose. The magnetic probe attracts the flexible member magnet to assist in retrieving the first end of the flexible member through the second nare of the nose. The system further includes a receiver for securing the nasal tube and possibly the flexible member externally, adjacent the nose to prevent dislodgement by the patient or otherwise. The receiver includes first and second pivotally connected portions forming a main body. Channels are provided for receiving the nasal tube and possibly the flexible member in a snap-fit manner.

22 Claims, 5 Drawing Sheets

U.S. PATENT DOCUMENTS

| | | |
|---|---|---|
| 3,896,527 A | 7/1975 | Miller et al. |
| 3,993,081 A | 11/1976 | Cussell |
| 4,176,756 A | 12/1979 | Gellman |
| 4,193,174 A | 3/1980 | Stephens |
| 4,244,362 A | 1/1981 | Anderson |
| 4,249,529 A | 2/1981 | Nestor et al. |
| 4,275,485 A | 6/1981 | Hutchison |
| 4,284,076 A | 8/1981 | Hall |
| 4,392,857 A | 7/1983 | Beran |
| 4,431,005 A | 2/1984 | McCormick |
| 4,458,385 A | 7/1984 | Espinoza |
| 4,514,882 A | 5/1985 | Lavielle |
| 4,634,425 A | 1/1987 | Meer |
| 4,775,121 A | 10/1988 | Carty |
| 4,778,448 A | 10/1988 | Meer |
| 4,913,139 A | 4/1990 | Ballew |
| 5,069,206 A | 12/1991 | Crosbie |
| 5,113,717 A | 5/1992 | Plamper |
| 5,115,542 A | 5/1992 | Gehres |
| 5,185,005 A | 2/1993 | Ballantyne |
| 5,226,892 A | 7/1993 | Boswell |
| 5,389,082 A | 2/1995 | Baugues et al. |
| 5,398,679 A | 3/1995 | Freed |
| 5,492,538 A | 2/1996 | Johlin, Jr. |
| 5,535,969 A | 7/1996 | Duffy, Jr. |
| 5,555,881 A | 9/1996 | Rogers et al. |
| 5,613,655 A | 3/1997 | Marion |
| 5,624,430 A | 4/1997 | Eton et al. |
| 5,782,236 A | 7/1998 | Ess |
| 5,795,335 A | 8/1998 | Zinreich |
| 5,806,516 A | 9/1998 | Beattie |
| 5,815,894 A | 10/1998 | Soriano |
| 5,817,103 A | 10/1998 | Bell |
| 6,029,668 A | 2/2000 | Freed |
| 6,067,985 A | 5/2000 | Islava |
| 6,394,092 B1 | 5/2002 | Barrett et al. |
| 6,631,715 B2 * | 10/2003 | Kirn ..................... 128/200.24 |

* cited by examiner

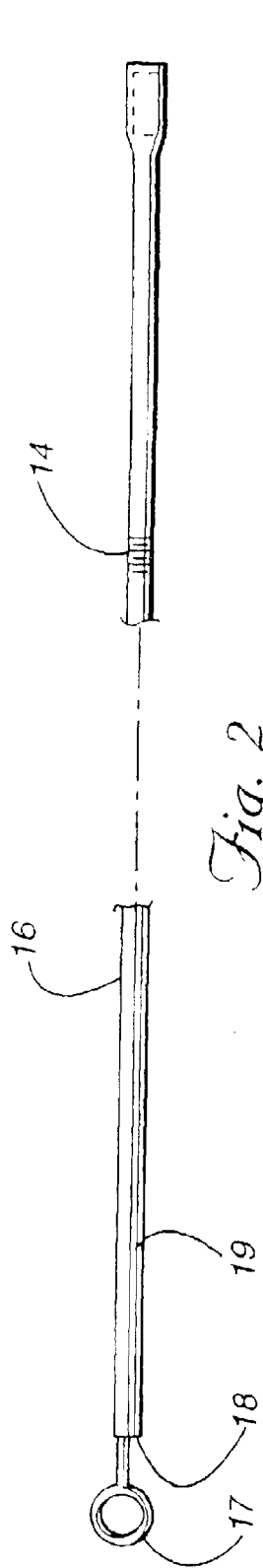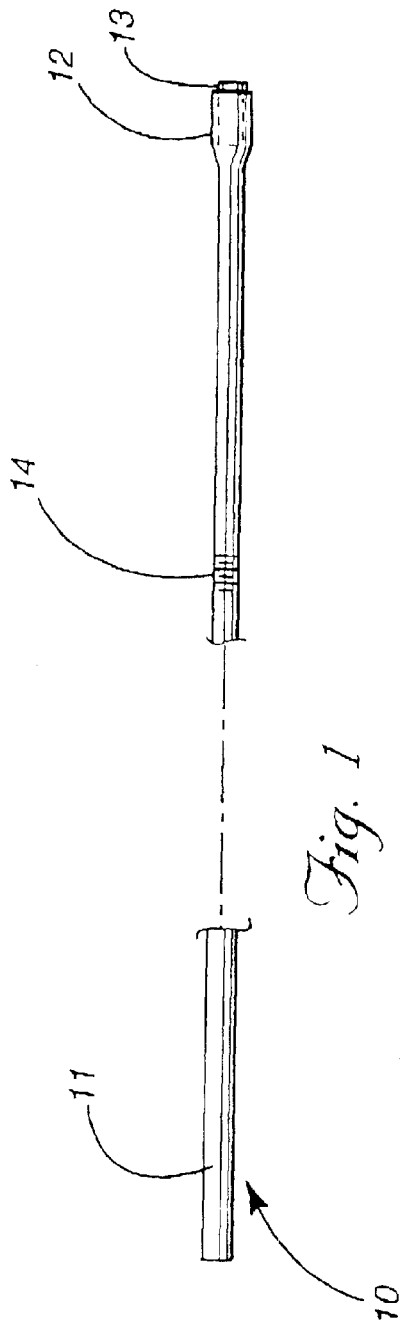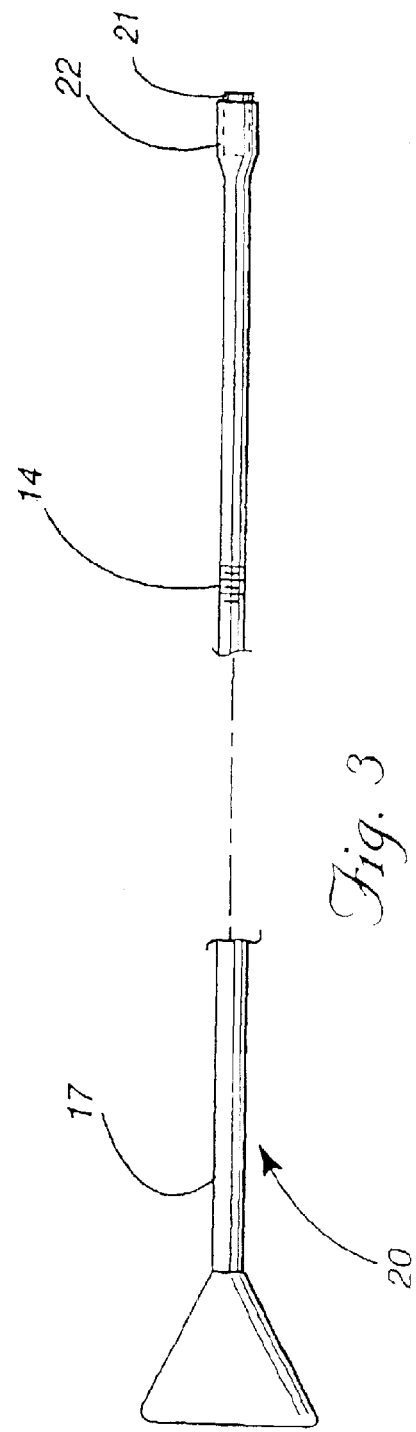

MAGNETIC NASAL TUBE BRIDLE SYSTEM AND RELATED METHOD

This is a continuation application of U.S. patent application Ser. No. 09/939,399, filed Aug. 24, 2001, now U.S. Pat. No. 6,631,715 entitled "Magnetic Nasal Tube Bridle System and Related Method."

TECHNICAL FIELD

The present invention relates generally to systems for placing and securing a nasal tube; and more particularly to such a system which utilizes magnets in the placement of a bridle used in combination with a receiver to secure the nasal tube.

BACKGROUND OF THE INVENTION

Many different methods have been used to place nasal tubes, such as feeding tubes, nasogastric tubes, and nasotracheal tubes into patients and to secure the tubes once placed. One such method disclosed in U.S. Pat. No. 5,185,005 to Ballantyne requires a bridle which is pulled into a nare of a patient's nose, around the posterior nasal septum, and out the other nare by a cord attached to the bridle and an insertion tool. Specifically, first and second installation tools are inserted into the nares of the patient's nose. Magnets associated with each tool couple together behind the posterior nasal septum. In the preferred embodiment, the pulling cord is attached to a magnetic assembly which is pulled free of its insertion tool by the removal of the remaining insertion tool. In this manner, removal of the second insertion tool pulls the bridle via the pulling cord through the first insertion tool and into a nare of the patient's nose, behind the nasal septum, and out of the other nare.

In an alternate embodiment described in the '005 patent, the bridle itself is associated with the magnet utilizing a fastening plate which is drilled and countersunk. The bridle is inserted through the drilled hole and knotted. The knot rests in the countersunk cavity of the fastening plate which is magnetically coupled to the magnet. Although the utilization of magnets to loop a bridle behind the nasal septum of a patient represents an advancement in the art, the apparatus described in the '005 patent includes numerous parts which are difficult to manufacture and time consuming to assemble. These difficulties increase the per unit cost of the apparatus and the opportunities for defects.

Prior to the '005 patent, U.S. Pat. No. 4,778,448 to Meer represented the state of the art. The '448 patent requires ends of a bridle to be inserted into first and second nares of a patient's nose until the ends are visible in the posterior pharynx of the patient. The visible ends of the bridle are then pulled out of the mouth of the patient using forceps or the like. The ends are then secured together forming a loop. The end of the loop adjacent the posterior nasal septum is then pulled such that the end of the loop protruding through the mouth is pulled back into the mouth, up the posterior pharynx and out of one of the nostrils. The harness is subsequently cut to a desired size such that the exterior end of the loop is adjacent the posterior nasal septum and rejoined. Although effective, the placement of the harness in this manner is both time consuming and difficult to undertake. Further, the process of placing the harness is uncomfortable for the patient and carries the risk of dislocation of the mandible since the patient's jaw must be opened widely to identify the ends of the harness in the posterior pharynx.

Additional methods for securing nasal tubes include attaching the tubes directly to the skin of the recipient utilizing an adhesive such as tape or the like, as described for example in U.S. Pat. Nos. 4,114,626 and 4,282,871, or sutures. All of these methods which rely on an adhesive to secure the feeding tubes have in common the disadvantages of being uncomfortable for the patient, gradually losing adhesion over time, risking injury to the underlying skin, or causing pressure necrosis of the nose itself from holding the tube tightly opposed to the nose.

Thus, as demonstrated by the limitations and disadvantages of the prior art methods for placing and securing nasal tubes in patients, there is a need identified for an improved bridle system and related method for placing and securing nasal tubes which allows rapid, easy looping of a bridle around the posterior nasal septum with minimal patient discomfort and no risk of mandibular dislocation. A need also exists for tools utilized to place the bridle which are few in number and simple to manufacture thus lowering the per unit cost of the bridle system such that the system may be pre-packaged and disposable. An additional need exists for a universal system capable of use with any type and/or size of nasal tube in order to limit the amount of storage space required in the medical facility.

SUMMARY OF THE INVENTION

The present invention meets these needs by providing an improved system for placing and securing at least one nasal tube in a patient comprising a flexible member having a first end portion for insertion into a first nare of a patient's nose and a second end portion, a first magnet secured substantially within the first end portion, a magnetic probe for insertion into a second nare of the nose for attracting the first magnet and retrieving the flexible member through the second nare, and a receiver for securing the tube and the flexible member once placed.

In accordance with a first aspect of the present invention, the receiver includes first and second pivotally connected portions forming a main body. A first channel having an opening along an axial direction thereof is formed in a first portion of the main body. At least portions of the channel opening, and preferably all of the opening, are smaller than an outer diameter of the tube for receiving and securing, or snapping, the tube into place. Additional channels may be formed in one or both portions of the main body for receiving the end portions of the flexible member.

In accordance with a second aspect of the present invention, an axis of the first channel may be offset from a line drawn through axes of the additional channels in order to minimize the size of the receiver. In addition, the receiver may be selected from a group of integrally molded receivers having first channels of different radii which allows the system to be utilized with any type and/or size nasal tube. Additional channels or recesses may be formed along exterior surfaces of one or both main body portions of the receiver for partially receiving the first, or additional nasal tubes, if desired. A fastener may also be provided for securing the tubes against the exterior surfaces of the receiver which are preferably smooth or contoured to prevent irritation of the patient's skin.

In accordance with another aspect of the present invention, the flexible member may be tubular and capable of receiving a rod or stylus inserted into a lumen thereof to provide additional rigidity during its insertion. Depending upon the initial rigidity of the flexible member, the rigidity of the stylus may vary and the stylus may even be unnecessary. In addition, the flexible member and/or the magnetic probe may include at least one indicia thereon indicating at least one insertion distance. The distance indicated by the indicia is preferably equal to an average distance from the nares to just beyond the choanal aperture.

According to yet another aspect of the present invention, a disposable kit for placing and securing a tube in a patient comprises a flexible member having first and second ends for insertion into a first nare of the patient's nose, a magnet attached to the first end of the flexible member, a magnetic probe for insertion into a second nare of the nose to attract the magnet and retrieve the magnet and the flexible member, and a group of integrally molded receivers for securing different types and/or sizes of tubes and the flexible member. Advantageously, the kit is self-contained with each of its component parts sterilized before placement therein.

In accordance with still another aspect of the present invention, a method for placing and securing a tube through a nose into a patient is provided. The method includes the steps of inserting at least one tube into a first or a second nare of the nose, inserting an end portion of a flexible member having a magnet substantially secured therein into the first nare of the nose, inserting a magnetic probe into the second nare of the nose for attracting the magnet/flexible member, removing the magnetic probe from the second nare of the nose thereby retrieving the end portion of the flexible member through the second nare of the nose, and securing the at least one tube and the flexible member. The step of securing the at least one tube may include the step of snapping the tube into a channel of a receiver. The method may further comprise the step of selectively removing the receiver from a group of integrally molded receivers for use in the securing step. The unselected receivers which may include spare receivers and/or receivers for use with different size tubes may be discarded.

Additional advantages, and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

BRIEF DESCRIPTION OF THE DRAWINGS

The accompanying drawings incorporated in and forming a part of the specification, illustrate several aspects of the present invention, and together with the description serve to explain the principles of the invention. In the drawings:

FIG. 1 is a perspective view of a flexible member for securing a nasal tube and having a magnet substantially secured within an end portion thereof;

FIG. 2 is a perspective view of an alternate flexible member for securing a nasal tube having a rod inserted into a lumen of the flexible member to provide additional rigidity during insertion of the flexible member;

FIG. 3 is a perspective view of a magnetic probe for attracting and coupling with a magnet attached to a flexible member and retrieving the flexible member;

Reference will now be made in detail to the present preferred embodiment of the invention, an example of which is illustrated in the accompanying drawings.

DETAILED DESCRIPTION OF THE PREFERRED EMBODIMENT

Figure 7A:
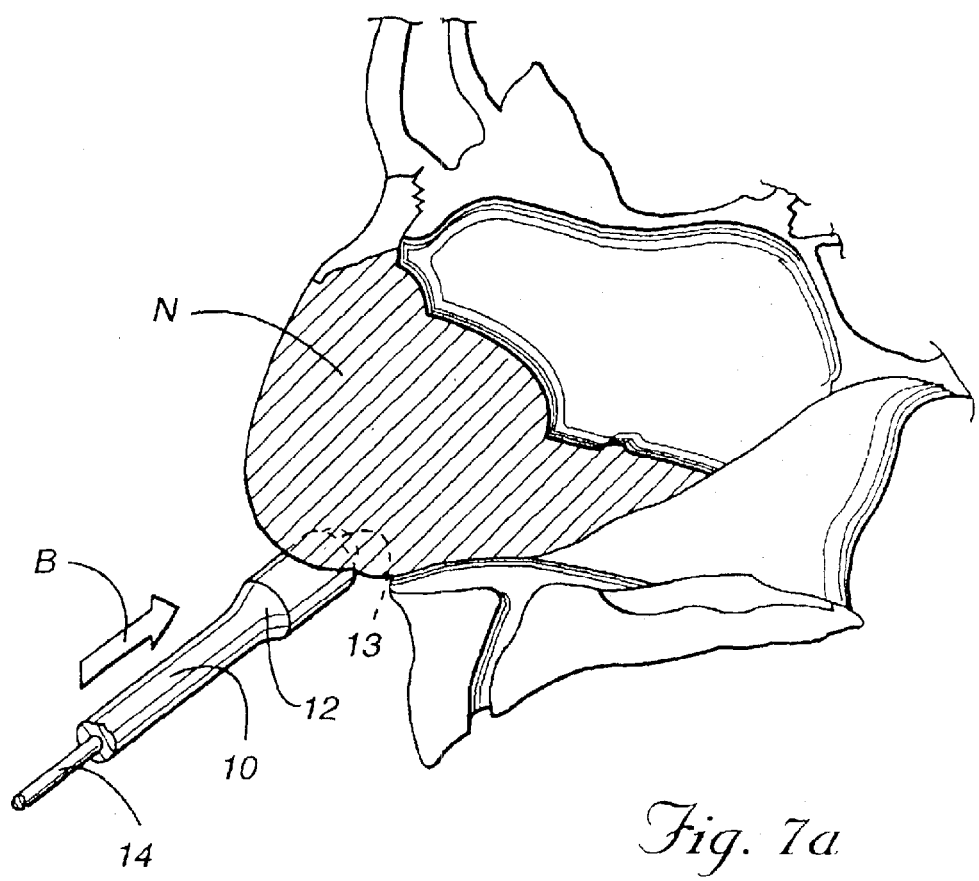
FIGS. 7a–7d are cross-sectional views showing: (a) the initial insertion of the first end portion of the flexible member into a first nare; (b) the first end portion of the flexible member inserted an average distance to a point just beyond the choanal aperture and the initial insertion of a magnetic probe into a second nare; (c) the removal of the probe magnetically coupled to the flexible member from the second nare of the nose; and (d) the flexible member after placement in the nose, trimming of the ends of the flexible member, placement of the nasal tube, and application of the receiver.
Figure 7B:
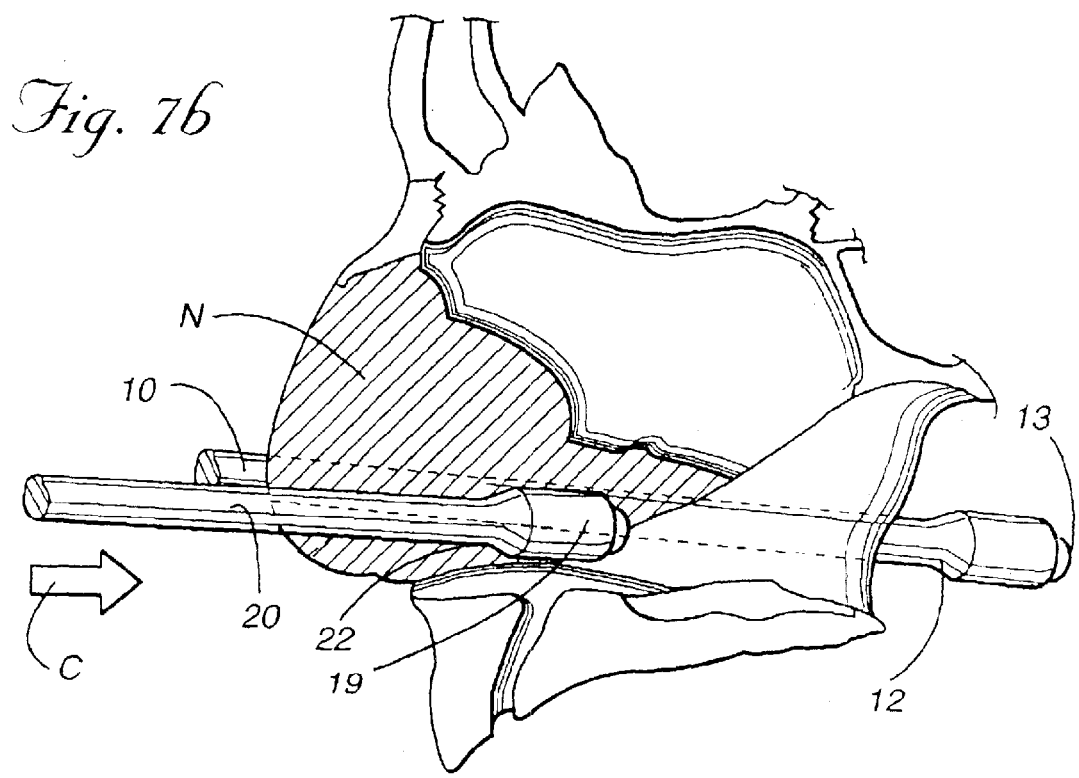

With reference to the perspective view of FIG. 1, there is shown a preferred embodiment of a flexible member 10 for use in placing and securing a nasal tube $T_1$ in a patient. The overall length of the flexible member 10 should be sufficient to allow a complete loop around the patient's nasal septum N such that end portions 11 and 12 of the flexible member 10 extend beyond first and second nares of the patient for securing the nasal tube $T_1$ as shown in FIG. 7d.

In the present preferred embodiment, the flexible member 10 or catheter consists of a soft flexible tube having a powerful rare-earth magnet 13 or a ferromagnetic cylinder attached to the end portion 12. Preferably, the end portion 12 of the flexible tube 10 is slid over the magnet 13 such that the magnet is substantially within the end portion 12. Alternatively, the flexible tube 10 may be molded around the magnet 13 thereby securing the magnet 13 in an integrated manner within the tube as shown in FIG. 2. Advantageously, either embodiment provides for smooth passage of the magnet 13 during its insertion and retrieval from the patient. Of course, other methods of securing the magnet 13 to the end portion 12 of the flexible tube 10, such as adhesives, tapes, etc. may be utilized in accordance with the broadest teachings of the present invention.

The flexible tube 10 may further include at least one indicia or mark 14, or a plurality of marks, indicating an average insertion distance. The distance indicated by the indicia 14 is preferably equal to an average distance from the nares to just beyond the choanal aperture within the nasal cavity. Advantageously, utilization of these marks substantially eliminates unnecessary contact with the posterior wall of the pharynx.

For relatively small diameter tubes 16 or catheters as shown in FIG. 2, a rod 17 or stylet may be inserted through a lumen 18 of an end portion 19 of the tube to provide additional rigidity during the insertion process. Depending upon the size and rigidity of the flexible tube 16, the rigidity of the rod 17 may vary.

With reference to the perspective view of FIG. 3, there is shown a magnetic probe 20 for insertion into a second nare of the patient's nose to attract the magnet 13 and retrieve the end portion 12 of the flexible tube 10. In the present preferred embodiment of the invention, the magnetic probe 20 consists of a rigid or semirigid plastic or rubber cylinder of relatively small diameter having a powerful rare-earth magnet 21 or ferromagnetic cylinder attached to a first end portion 22. Preferably, the probe 20 is sized for receiving the magnet 21 in a force fit manner or integrally molded around the magnet 21 such that the magnet is secured in an integrated manner within the probe. Of course, other methods of attaching the magnet 21 to the end portion of the magnetic probe 20, such as adhesives, tapes, etc. may be utilized in accordance with the broadest teachings of the present invention. In order to attract the magnet 13 attached to the end portion 12 of the flexible tube 10, the polarity of the probe magnet 21 is selected to be opposite that of the magnet 13. The length of the magnetic probe 20 must be sufficient to reach from the nare beyond the choanal aperture while still being grasped by the operator's hand or a suitable instrument.

Figure 4:
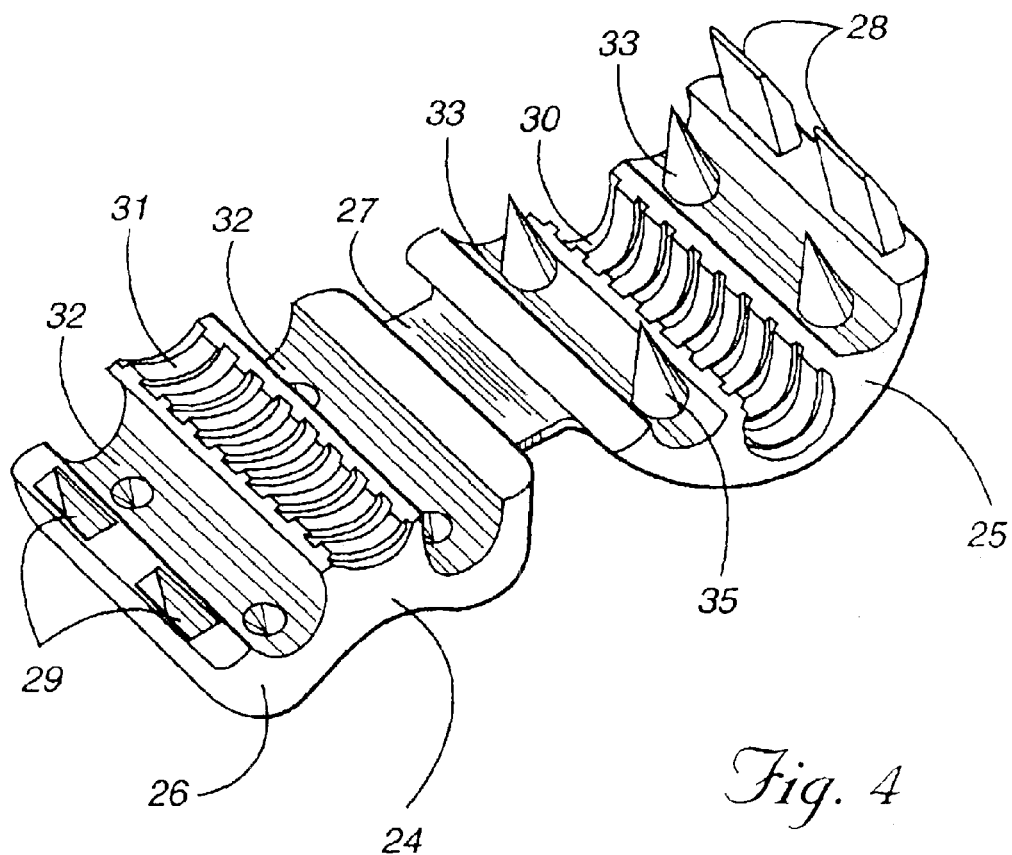
FIG. 4 is a perspective view of a receiver shown in an open position for receiving and securing a nasal tube and ends of a flexible member.
Figure 5:
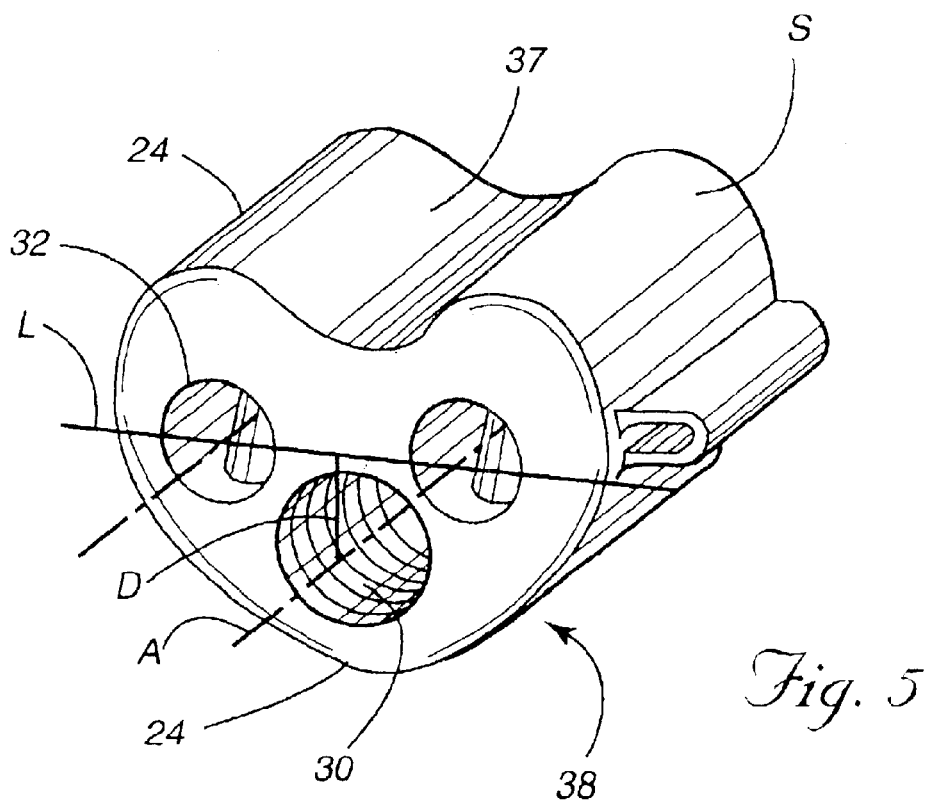
FIG. 5 is a perspective view of a receiver for securing a nasal tube and ends of a flexible member.

With reference to FIGS. 4 and 5, there is shown a receiver 24 for securing the nasal tube $T_1$ and the end portions 11 and 12 of the flexible tube 10. In the present preferred embodiment of the invention, the receiver 24 consists of a molded plastic main body having first and second pivotally connected members or portions 25 and 26. The members 25 and 26 are connected by a living hinge 27 formed during molding of the receiver 24. Integrally formed snap-type locking hooks 28 extend from member 25 and mating holes 29 are formed in member 26 for firmly securing the members together following placement of the nasal tube $T_1$ and end portions 11 and 12 therein during use. Of course, other known means for securing the members 25 and 26 together during use may be used in accordance with the broadest teaching of the invention.

The preferred receiver 24 further includes a first channel 30 formed in member 25 for receiving the nasal tube $T_1$. Preferably, the channel 30 includes an opening along an axial direction thereof which is smaller along at least portions of its length than an outer diameter of the nasal tube $T_1$ for securing the tube in the channel. In other words, the size of the axial opening allows the nasal tube $T_1$ to be snapped into place. Advantageously, this significantly simplifies the placement of the nasal tube $T_1$ within the receiver 24 during installation. A mating channel 31 may be formed in member 26. Preferably, the channels 30 and 31 form a hole through the receiver 24 which firmly grasps the exterior of the nasal tube $T_1$ to prevent dislodgement by the patient or otherwise and without occluding the lumen of the tube.

The preferred receiver 24 further includes first and second channels 32 formed in member 26 for receiving the flexible tube 10. Preferably, the channels 32 include openings along an axial direction thereof which are smaller along at least portions of their length than an outer diameter of the flexible tube 10 for securing the end portions 11 and 12 of the tube in the channels. In other words, the size of the axial opening allows the end portions 11 and 12 of the flexible tube 10 to be snapped into place. Again, this significantly simplifies the placement of the flexible tube 10 within the receiver 24 during installation. Mating channels 33 may be formed in member 25. Preferably, the channel pairs 32 and 33 form holes through the receiver 24 which firmly grasp the exterior of the flexible tube 10 to prevent dislodgement by the patient or otherwise. Additional means, such as barbs 35 in the preferred embodiment, may be used to impinge the exterior of the nasal tube $T_1$ or end portions 11 and 12 of the flexible tube 10 to further assist in the prevention of their dislodgement during use.

As best shown in FIG. 5, the three channels 30 and 32 in the preferred embodiment are non-linear. In other words, an axis A of the channel 30 is offset a distance D from a line L drawn through axes of channels 32. In accordance with an important aspect of the present invention, this allows the receiver 24 to be smaller and therefore less intrusive to a patient than a receiver utilizing a linear arrangement. Additional advantages of the preferred receiver include rounded or contoured exterior surfaces which provide a smooth contact surface for the patient to prevent irritation and an additional recess or channel 37 formed in the exterior surface S, for example, for receiving an additional and possibly oversized tube (not shown). In this manner, a secondary nasal tube (not shown) perhaps having a large diameter can be easily secured against the exterior surface of the receiver 24 using a plastic binding strap (not shown), for example, which may be integrated with the receiver 24 to facilitate its securement. Of course, other methods for securing tubes against the receiver 24, such as snap-fit recesses or channels, adhesives, tapes, etc. may be utilized in accordance with the broad teachings of the present invention.

Figure 6:
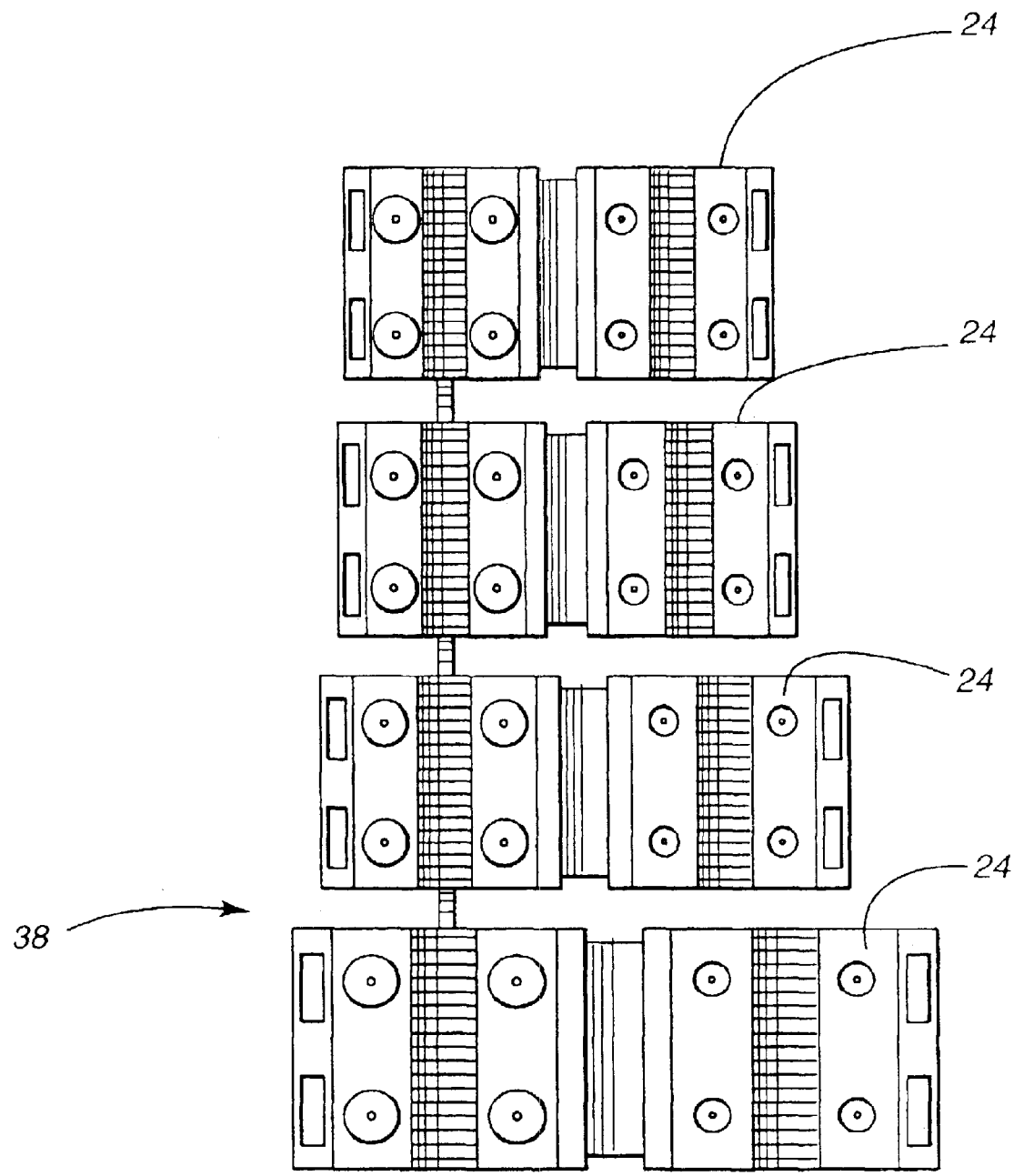
FIG. 6 is a top view of a group of four integrally molded receivers from which a receiver for securing a nasal tube and ends of a flexible member is selected.

As further shown in FIG. 6, the receiver 24 may include a group of integrally molded receivers 38. Although four such receivers 24 are shown in FIG. 6, any number of receivers may be attached one to another in accordance with the present invention. The integrally molded receivers 38 may include receivers 24 designed to accommodate different size nasal tubes or even spare receivers of the same size and may be attached one to another at any location on their respective exterior surfaces.

The present preferred method of placing and securing a tube in a patient includes the steps of inserting the tube into a nare of the patient's nose, inserting an end portion 12 of a flexible member 10 into a first nare of the patient's nose, inserting a magnetic probe 20 into a second nare of the nose for attracting the end portion of the flexible member, removing the magnetic probe 20 from the second nare of the nose thereby retrieving the end portion of the flexible member through the nare, and securing the tube and end portions of the flexible member.

Prior to insertion into the patient, the tube $T_1$, the end portion 12 of the flexible member 10, and the magnetic probe 20 are preferably lubricated with a biologically compatible lubricant. For the comfort of an awake patient, a nasal anesthetic may also be applied. As shown by action arrow B in FIG. 7a, the end portion 12 of the flexible member 10 attached to the magnet 13 is inserted into a first nare of the nose. The flexible member 10 is threaded along a floor of the nose until the end portion 12 of the flexible member and magnet 13 have passed just beyond the posterior border of the nasal septum N through the choanal aperture as shown in FIG. 7b. Preferably, the approximate depth of insertion of the flexible member 10 is indicated by one or more indicia 14 on the flexible member 10. Less preferably, the practitioner may rely on resistance encountered when the end portion 12 of the flexible member and magnet 13 reach the posterior wall of the pharynx as an indicator.

At this point, the magnetic probe 20 is similarly inserted into a second nare of the nose as shown by action arrow C in FIG. 7b. The magnetic probe 20 attracts and connects with the magnet 13 attached to the end portion 12 of the flexible member 10 thus allowing the end portion of the flexible member to be retrieved through the second nare of the nose. The magnetic probe 20 is preferably inserted in a substantially parallel course to that of the flexible member 10 along the nasal floor. When the magnetic probe 20 has been inserted to an appropriate depth which may be indicated by indicia 18 on the probe, the magnet 13 attached to the end portion 12 of the flexible member 10 is attracted to the magnetic probe 20.

Figure 7C:
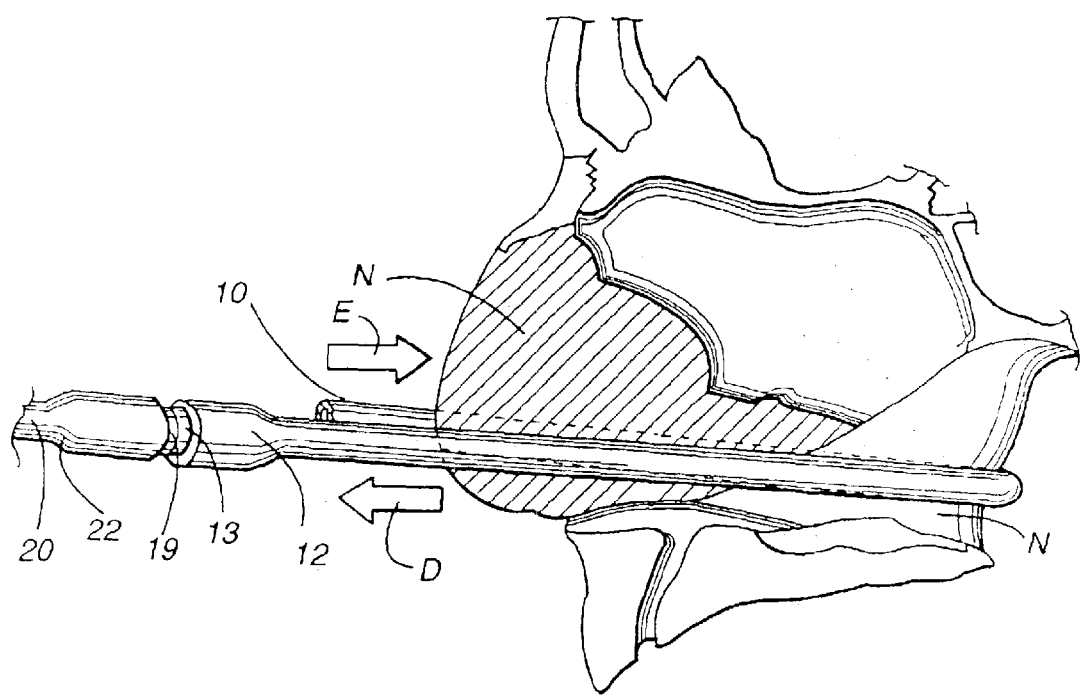
Figure 7D:
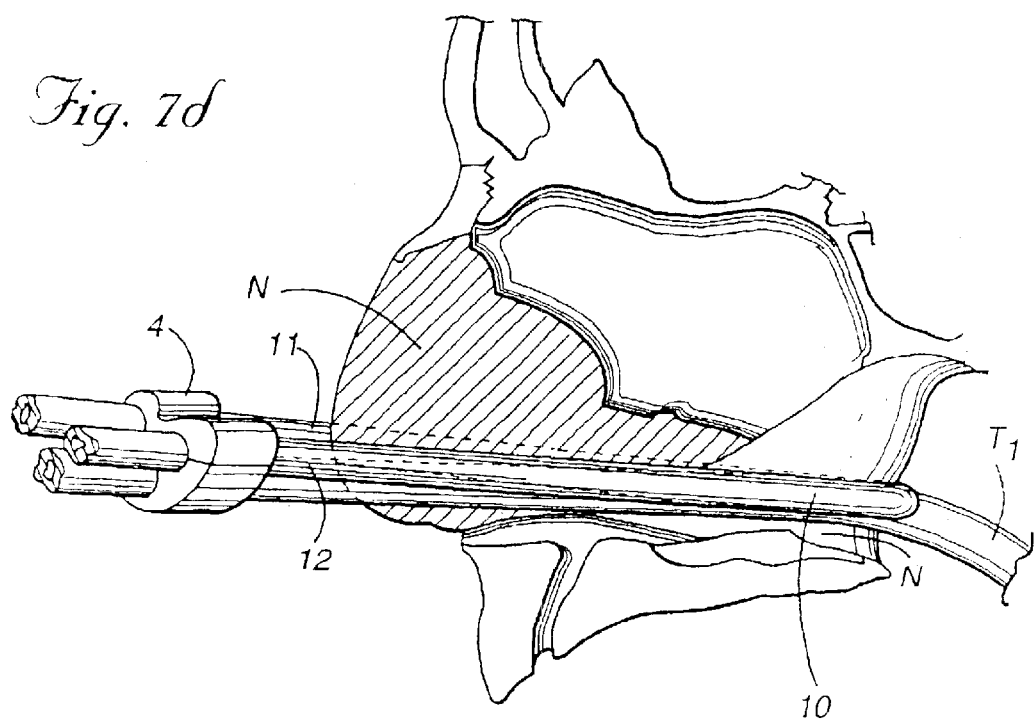

As shown by action arrow D in FIG. 7c, the magnetic probe 20 is then withdrawn from the second nare of the patient's nose, pulling the magnetically coupled flexible member 10 into the first nare and out through the second nare (shown by action arrows E and D in FIG. 7c). Hence, the flexible member 10 is now looped around the nasal septum N posteriorly as shown in FIGS. 7c and 7d.

The magnet 13 and the magnetic probe 20 are then separated and the first end portion 12 of the flexible member 10 and magnet 13 are trimmed to a suitable length. The receiver 24 is then secured to the end portions 11, 12 of the flexible member extending from the nares, as well as the nasal tube(s) $T_1 \ldots T_n$ such that a sufficient distance is provided between the nose and the receiver 24 to avoid contact with the patient's nose. In the present preferred method, the step of securing the tube $T_1$ includes the step of snapping the tube into a channel 30 formed in the receiver 24. Of course, in accordance with the broad teachings of the present invention, the nasal tube $T_1$ is similarly inserted in either nare before or after the above steps are performed.

In an alternate embodiment of the present invention, the method may include the additional step of selectively removing a receiver 24 from a group of integrally molded receivers 38 for use in the securing step. The unselected receivers 24 which may include spare receivers and/or receivers for use with different size tubes are preferably discarded.

The foregoing description of the preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A bridle system for placing and securing at least one tube in a patient comprising:
    a member having first and second ends, said first end for insertion into a first nare of a nose;
    a magnet secured within said first end;
    a magnetic probe for insertion into a second nare of the nose to attract said magnet and retrieve said magnet and said first end of said member; and
    a receiver for securing the at least one tube.

2. The bridle system for placing and securing at least one tube in claim 1, wherein said receiver secures at least one of the at least one tube and said first and second ends of said member.

3. The bridle system for placing and securing at least one tube in claim 1, wherein said receiver secures the at least one tube and said first and second ends of said member.

4. The bridle system for placing and securing at least one tube in claim 1, wherein said receiver includes first and second pivotally connected portions.

5. The bridle system, for placing and securing at least one tube in claim 1, wherein said member is tubular.

6. The bridle system for placing and securing at least one tube in claim 5, wherein said receiver secures at least one of the at least one tube and said first and second ends of said member.

7. The bridle system for placing and securing at least one tube in claim 5, wherein said receiver secures the at least one tube and said first and second ends of said member.

8. A bridle system for placing and securing at least one tube in a patient comprising:
    a flexible member having first and second ends, said first end for insertion into a first nare of a nose;
    a magnet secured within said first end;
    a probe for insertion into a second nare of the nose to attract said magnet and retrieve said magnet and said first end of said flexible member; and
    a receiver for securing the at least one tube.

9. The bridle system for placing and securing at least one tube in claim 8, wherein said receiver secures at least one of the at least one tube and said first and second ends of said flexible member.

10. The bridle system for placing and securing at least one tube in claim 8, wherein said receiver secures the at least one tube and said first and second ends of said flexible member.

11. The bridle system for placing and securing at least one tube in claim 8, wherein said receiver includes first and second pivotally connected portions.

12. The bridle system for placing and securing at least one tube in claim 8, wherein said flexible member is tubular.

13. The bridle system for placing and securing at least one tube in claim 12, wherein said receiver secures at least one of the at least one tube and said first and second ends of said flexible member.

14. The bridle system for placing and securing at least one tube in claim 12, wherein said receiver secures the at least one tube and said first and second ends of said flexible member.

15. A bridle system for placing and securing at least one tube in a patient comprising:
    a member having first and second ends, said first end for insertion into a first nare of a nose;
    a magnet secured substantially within said first end;
    a magnetic probe for insertion into a second nare of the nose to attract said magnet and retrieve said magnet and said first end of said member; and
    a receiver for securing the at least one tube.

16. The bridle system for placing and securing at least one tube in claim 15, wherein said receiver secures at least one of the at least one tube and said first and second ends of said member.

17. The bridle system for placing and securing at least one tube in claim 15, wherein said receiver secures the at least one tube and said first and second ends of said member.

18. The bridle system for placing and securing at least one tube in claim 15, wherein said member is flexible.

19. The bridle system for placing and securing at least one tube in claim 18, wherein said receiver secures at least one of the at least one tube and said first and second ends of said flexible member.

20. A bridle system for placing and securing at least one tube in a patient comprising:
    a flexible member having first and second ends, said first end for insertion into a first nare of a nose;
    a magnet attached to said first end of said flexible member;
    a probe for insertion into a second nare of the nose to attract said magnet and retrieve said magnet and said first end of said member; and
    a receiver for securing the at least one tube.

21. The bridle system for placing and securing at least one tube in claim 20, wherein said receiver secures at least one of the at least one tube and said first and second ends of said flexible member.

22. The bridle system for placing and securing at least one tube in claim 20, wherein said flexible member is tubular, and said receiver secures at least one the at least one tube and said first and second ends of said flexible member.

* * * * *